United States Patent

Nagase et al.

[11] 3,989,750
[45] Nov. 2, 1976

[54] RACEMIZATION OF OPTICALLY ACTIVE 2,2-DIMETHYL-3-(1'-ALKENYL)-CYCLOPROPANE-1-CARBOXYLIC ACIDS

[75] Inventors: Tsuneyuki Nagase; Gohu Suzukamo, both of Osaka, Japan

[73] Assignee: Sumitomo Chemical Company, Limited, Osaka, Japan

[22] Filed: Nov. 8, 1974

[21] Appl. No.: 522,130

[30] Foreign Application Priority Data
Nov. 12, 1973  Japan............................. 48-127502

[52] U.S. Cl. .................... 260/544 L; 260/514 H
[51] Int. Cl.² ................................. C17C 61/18
[58] Field of Search ................ 260/544 L, 514 H

[56] References Cited
UNITED STATES PATENTS
3,794,680   2/1974   Matsui et al. .................. 260/514

Primary Examiner—Robert Gerstl
Attorney, Agent, or Firm—Stewart and Kolasch, Ltd.

[57] ABSTRACT

A method for racemization of optically active 2,2-dimethyl-3-(1'-alkenyl)-cyclopropane-1-carboxylic acids of the formula:

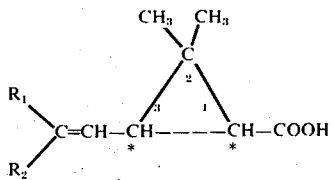

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms, which comprises the step of contacting the corresponding acid halide with a Lewis acid.

9 Claims, No Drawings

RACEMIZATION OF OPTICALLY ACTIVE 2,2-DIMETHYL-3-(1'-ALKENYL)-CYCLOPROPANE-1-CARBOXYLIC ACIDS

The present invention relates to a method for racemization of optically active 2,2-dimethyl-3-(1'-alkenyl)-cyclopropane-1-carboxylic acids.

More particularly, it relates to a method for racemization of optically active 2,2-dimethyl-3-(1'-alkenyl)-cyclopropane-1-carboxylic acids represented by the formula:

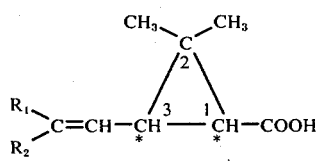

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms, which comprises the step of contacting the corresponding acid halide represented by the formula:

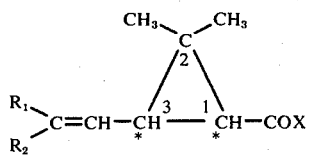

wherein X is a halogen atom and $R_1$ and $R_2$ are each as defined above with a Lewis acid.

Among the cyclopropanecarboxylic acids represented by the formula [I], 2,2-dimethyl-3-(2'-methyl-1'-propenyl)-cyclopropane-1-carboxylic acid is popularly named as chrysanthemic acid and known to be the acid component of esters which are useful as pyrethroidal insecticides exhibiting an immediate effect with little toxicity such as pyrethrin, allethrin and phthalthrin. It is also known that esters of 2,2-dimethyl-3-vinyl-cyclopropane-1-carboxylic acid, 2,2-dimethyl-3-cyclopentylidenemethyl-cyclopropane-1-carboxylic acid, 2,2-dimethyl-3-cyclohexylidenemethyl-cyclopropane-1-carboxylic acid and the like exhibit an immediate insecticidal activity with little toxicity.

The cyclopropanecarboxylic acids [I] have four optical isomers, i.e. two geometrical ones (cis form and trans form) and two optical ones ((+) form and (−) form) for each of them. Among the esters derived from these isomeric carboxylic acids, the trans isomer possesses a stronger activity than the corresponding cis isomer. Further, the (+) isomer exhibits a much higher effect than the corresponding (−) isomer.

In general, the cyclopropanecarboxylic acids [I] are industrially produced in the form of a racemic modification (i.e. (±) form), which comprises the cis isomer and the trans isomer. This racemic modification is then subjected to optical resolution with an optically active organic base to isolate the (+) isomer which is useful. The remaining (−) isomer, which does not have any practical value, may be subjected to racemization and optical resolution to obtain additionally the useful (+) isomer. Thus, an efficient method for such racemization is industrially of great significance.

As shown in the above mentioned formula, the optically active cyclopropanecarboxylic acids [I] have two asymmetric carbon atoms at the 1- and 3-positions so that racemization of them is very difficult. Epimerization at the $C_1$-position alone is comparatively easier than the racemization, and there are known several methods for such epimerization, of which examples are contacting an alkyl ester of cis-chrysanthemic acid with a specific basic catalyst under heating to obtain trans-chrysanthemic acid [Japanese Patent Publication No. 6457/1965], heating cis-pyrethrinic acid chloride at a high temperature [Japanese Patent Publication No. 24694/1971], etc. According to these methods, however, epimerization at both asymmetric carbon atoms can not be attained, and only the conversion of (−)-cis-chrysanthemic acid into (+)-trans-chrysanthemic acid or of (+)-cis-chrysanthemic acid into (−)-trans-chrysanthemic acid is brought about. Since these methods are based on higher thermodynamical stability of the trans isomer in comparison with the cis isomer, the conversion of the (−)-trans isomer into the (+)-trans isomer is not attained by them and may be accomplished only by changing the former to the (−)-cis isomer through complicated processes and epimirizing the resulting product at the $C_1$-position.

On the other hand, extensive studies for realization of the racemization have been made and, as the results, some procedures for the racemization have been already proposed. Typical examples of them include a method in which the alkenyl group at the $C_3$-position in (−)-trans-chrysanthemic acid is converted into a keto-alcohol group and the acid group at the $C_1$-position is converted into a lower alkyl ester, which is then treated with an alkali metal alcoholate in a solvent [Japanese Patent Publication No. 15977/1964] and a method in which (−)-trans-chrysanthemic acid is irradiated with ultraviolet rays in the presence of a photosensitizer [Japanese Patent Publication No. 30697/1972]. However, the former method is industrially disadvantageous because many reaction steps are required. The latter method is insufficient in reaction efficiency and is uneconomical because of the large consumption of electric power for the light source. Thus, these conventional racemization processes comprise the chemical conversion of the alkenyl group at the $C_3$-position into a keto-alcohol group, which has chemically the same property as the carbonyl group at the $C_1$-position, and the subsequent epimerization at both the $C_1$- and $C_3$-positions at the same time by the use of a strong base, or the application of a high energy sufficient for cleavage of the cyclopropane ring.

As the result of an extensive study, it has now been surprisingly found that the racemization of the optically active cyclopropanecarboxylic acid [I] occurs readily at moderate temperature by contacting an acid halide of the carboxylic acid with a Lewis acid. This invention is based on such finding.

According to the present invention, the optically active cyclopropane carboxylic acid [I] is subjected to racemization in an acid halide form, usually in an acid chloride form. The acid halide may be prepared by a conventional procedure. For example, the acid chloride can be obtained by reacting the carboxylic acid with a chlorinating agent such as thionyl chloride, sulfuryl chloride, phosphoric chloride, phosphorous chloride or the like. The thus obtained acid halide is then contacted with a catalytic amount of a Lewis acid, particularly a metal halide type Lewis acid such as aluminum chloride, aluminum bromide, ferric chloride, stannic chloride, titanium chloride, boron trichloride, boron trifluoride, zinc chloride or the like whereby racemization occurs irrespective of the external pressure without any trouble in the reaction. In the racemization reaction, any of the four optical isomers can be used solely or in the combination in an optical proportion as the starting material. The racemization can be attained irrespective of their optical purities.

The racemization may be performed batchwise or continuously. The optically active cyclopropanecarboxylic acid halide may be introduced in the whole amount from the start together with the catalyst into a reactor. If desired, it may be introduced into the reactor successively or intermittently depending on the proceeding of the racemization.

The reaction is favorably carried out in the presence of a solvent which does not afford any unfavorable influence on the proceeding of the racemization. An ether (e.g. diethyl ether, dioxane, ethylene glycol dimethyl ether), an aromatic solvent (e.g. benzene, toluene, xylene, chlorobenzene), an aliphatic hydrocarbon (e.g. hexane, heptane) or a halogen-substituted aliphatic hydrocarbon (e.g. chloroform, 1,1,2,2-tetrachloroethane, trichloroethylene) may be employed as the solvent.

The catalyst may be used in an amount of about 1/2000 to 1/2 mol, preferably about 1/200 to 1/10 mol, to 1 mol of the optically active cyclopropanecarboxylic acid halide.

The reaction temperature is usually from about 20° C to the boiling temperature of the reaction system, favorably from about 40° to 120° C.

The reaction time is more or less associated with the amount of the catalyst and the reaction temperature. Usually, the racemization is sufficiently accomplished within about 10 minutes to 20 hours.

After completion of the reaction, the recovery of the racemized product may be carried out by a conventional separation procedure. For instance, the reaction mixture is treated with an aqueous alkaline solution for hydrolysis and then neutralized with a mineral acid, whereby a pure, completely racemized cyclopropanecarboxylic acid can be obtained.

If desired, the racemized cyclopropanecarboxylic acid halide can be, without hydrolysis, directly subjected to the reaction with an alcohol which is popularly named as pyrethrolone, allethrolone or the like in the presence of a hydrogen halide-eliminating agent to obtain an ester having an insecticidal activity.

By the method of the invention, the racemization of the (—) isomer of the optically active chrysanthemic acid can be readily accomplished. The thus racemized product may be subjected to optical resolution to obtain the useful (+) isomer of chrysanthemic acid.

Practical and presently preferred embodiments of the invention are illustratively shown in the following Examples.

EXAMPLE 1

In a 300 ml flask, there were charged n-pentane (100 ml) and (—)-trans-2,2-dimethyl-3-isobutenylcyclopropane-1-carboxylic acid (50.0 g), and thionyl chloride (46.0 g) was added thereto from a dropping funnel in 20 minutes with stirring under reflux. After completion of the addition, stirring was continued for a further 3 hours, and then the solvent and excess of the thionyl chloride were removed by distillation. The residue was distilled to give (—)-trans-2,2-dimethyl-3-isobutenylcyclopropane-1-carboxylic acid chloride (53.9 g) having a boiling point of 50° C/0.5 mmHg - 56° C/0.6 mmHg. Other cyclopropanecarboxylic acid halides were prepared in the same manner as above.

EXAMPLE 2

In a 500 ml flask equipped with a calcium chloride-tube, there were charged (—)-trans-2,2-dimethyl-3-isobutenylcyclopropane-1-carboxylic acid chloride (40.0 g) and dioxane (160 g), and anhydrous aluminum chloride (0.86 g) was added thereto. The contents were stirred at 70° C for 4 hours. Then, a small amount of water was added thereto to deactivate the catalyst, and the solvent was distilled off. The residue was hydrolyzed with an aqueous solution of sodium hydroxide in a conventional manner. The hydrolyzed product was acidified with 20 % sulfuric acid and extracted with n-hexane. The n-hexane extract was washed with water and dried. After removal of the solvent by distillation, the residue was distilled to give an oil (32.4 g) having a boiling point of 103° to 110° C/0.8 mmHg, which crystallized immediately. M.P. 48° to 52° C. The IR absorption spectrum of this product was identical with that of (+)-2,2-dimethyl-3-isobutenylcyclopropane-1-carboxylic acid. The composition of this product determined by gas chromatographic analysis was as follows:

| Optical isomer | (+)-trans | (—)-trans | (+)-cis | (—)-cis |
|---|---|---|---|---|
| Content (% by weight) | 45.7 | 45.5 | 4.4 | 4.4 |

EXAMPLE 3

In a 50 ml flask, there were charged (+)-cis-2,2-dimethyl-3-isobutenylcyclopropane-1-carboxylic acid chloride (10.2 g) and dioxane (40 g), and anhydrous aluminum chloride (0.43 g) was added thereto. The contents were stirred at 67° to 70° C. With lapse of the reaction time, a part of the reaction mixture was taken out and subjected to gas chromatographic analysis whereby the following results were obtained:

| Reaction time (min.) | Optical isomers (% by weight) | | | |
|---|---|---|---|---|
| | (+)-trans | (—)-trans | (+)-cis | (—)-cis |
| Starting material | 0 | 0 | 100 | 0 |
| 10 | 48.3 | 40.9 | 6.2 | 4.6 |
| 30 | 44.1 | 44.4 | 6.0 | 5.4 |
| 60 | 45.2 | 45.8 | 4.8 | 4.2 |
| 120 | 45.5 | 45.6 | 4.5 | 4.4 |

After completion of the reaction, the reaction mixture was treated as in Example 2 to give (+)-2,2-dimethyl-3-isobutenylcyclopropane-1-carboxylic acid (7.4 g).

EXAMPLE 4

In a 1000 ml flask, there were charged levo-rotatory cis- and trans-2,2-dimethyl-3-isobutenylcyclopropane-1-carboxylic acid chloride (composition: (+)-trans, 12.6 % by weight; (—)-trans, 67.8 % by weight; (+)-cis, 2.7 % by weight; (—)-cis, 16.9 % by weight) (100.0 g)

and dioxane (400 g), and anhydrous aluminum chloride (3.5 g) was added thereto. The contents were stirred at 68 to 69° C. With lapse of the reaction time, a part of the reaction mixture was taken out and subjected to gas chromatographic analysis whereby the following results were obtained:

| Reaction time (min.) | Optical isomers (% by weight) | | | |
|---|---|---|---|---|
| | (+)-trans | (−)-trans | (+)-cis | (−)-cis |
| Starting material | 12.6 | 67.8 | 2.7 | 16.9 |
| 30 | 24.6 | 63.4 | 4.5 | 7.6 |
| 120 | 38.9 | 48.5 | 6.0 | 6.6 |
| 180 | 43.5 | 44.4 | 5.5 | 6.6 |
| 240 | 44.7 | 45.0 | 5.0 | 5.3 |

After completion of the reaction, the reaction mixture was treated as in Example 2 to give (+)-2,2-dimethyl-3-isobutenylcyclopropane-1-carboxylic acid (81.5 g).

EXAMPLE 5

As in Example 4, the racemization was carried out at 50° C. After 10 hours, the completion of the reaction was confirmed by gas chromatographic analysis. The reaction mixture was treated as in Example 4 to give (+)-2,2-dimethyl-3-isobutenylcyclopropane-1-carboxylic acid (80.1 ).

EXAMPLE 6

In a 100 ml flask, there were charged (−)-trans-2,2-dimethyl-3-isobutenylcyclopropanecarboxylic acid chloride (5.0 g) and dioxane (45 g), and anhydrous aluminum chloride (0.20 g) was added thereto. The contents were stirred at 80° C for 1 hour. Then, the catalyst was deactivated, and the solvent was distilled off. The residue was distilled under reduced pressure to give racemized 2,2-dimethyl-3-isobutenylcyclopropane-1-carboxylic acid chloride having a boiling point of 50° − 54° C/0.6 mmHg (4.4 g).

EXAMPLE 7

In a 1000 ml flask, there were charged levo-rotatory cis- and trans-2,2-dimethyl-3-isobutenylcyclopropane-1-carboxylic acid chloride (composition: (+)-trans, 14.0 % by weight; (−)-trans, 65.8 % by weight; (+)-cis, 2.9 % by weight, (−)-cis, 17.4 % by weight) (42.0 g) and toluene (378 g), and ferric chloride (1.85 g) was added thereto. The contents were stirred at 70° C. With lapse of the reaction time, a part of the reaction mixture was taken out and subjected to gas chromatographic analysis whereby the following results were obtained:

| Reaction time (min.) | Optical isomers (% by weight) | | | |
|---|---|---|---|---|
| | (+)-trans | (−)-trans | (+)-cis | (−)-cis |
| Starting material | 14.0 | 65.8 | 2.9 | 17.4 |
| 60 | 36.4 | 54.0 | 4.6 | 4.9 |
| 120 | 43.0 | 46.3 | 5.6 | 5.1 |

After completion of the reaction, a small amount of water was added thereto to deactivate the catalyst, and the solvent was distilled off. The residue was hydrolyzed with an aqueous solution of sodium hydroxide in a conventional manner. The hydrolyzed product was acidified with 20 % sulfuric acid and extracted with toluene. The toluene extract was washed with water and the solvent was removed by distillation. The residue was distilled to give an oil (30.8 g) having a boiling point of 103 to 110° C/0.8 mmHg, which crystallized immediately. M.P. 48° − 52° C.

EXAMPLE 8

In a 1000 ml flask, there were charged levo-rotatory cis- and trans-2,2-dimethyl-3-isobutenylcyclopropane-1-carboxylic acid chloride (composition: (+)-trans, 14.8 % by weight; (−)-trans, 65.0 % by weight; (+)-cis, 2.9 % by weight; (−)-cis, 17.3 % by weight) (60.5 g) and toluene (547 g), and anhydrous aluminum chloride (2.2 g) was added thereto. The contents were stirred at 68 to 70° C for 5 hours. The reaction mixture was treated as in Example 7 to give (+)-2,2-dimethyl-3-isobutenylcyclopropane-1-carboxylic acid (43.2 g) having a boiling point of 127° − 135° C/4 mmHg (composition: (+)-trans, 43.2 % by weight; (−)-trans, 46.2 % by weight; (+)-cis, 5.1 % by weight; (−)-cis, 5.7 % by weight).

EXAMPLE 9

In a 200 ml flask, there were charged levo-rotatory cis- and trans-2,2-dimethyl-3-isobutenylcyclopropane-1-carboxylic acid chloride (8.6 g) and monochlorobenzene (78 g), and anhydrous aluminum chloride (0.31 g) was added thereto. The contents were stirred at 70° C. With lapse of the reaction time, a part of the reaction mixture was taken out and subjected to gas chromatographic analysis whereby the following results were obtained:

| Reaction time (min.) | Optical isomers (% by weight) | | | |
|---|---|---|---|---|
| | (+)-trans | (−)-trans | (+)-cis | (−)-cis |
| Starting material | 13.9 | 66.1 | 2.8 | 17.2 |
| 10 | 31.3 | 57.4 | 4.9 | 6.5 |
| 30 | 36.3 | 52.7 | 4.9 | 6.2 |
| 60 | 39.3 | 49.4 | 5.1 | 6.3 |
| 120 | 41.1 | 47.9 | 5.1 | 6.0 |
| 180 | 42.7 | 46.1 | 5.2 | 6.0 |

After completion of the reaction, the reaction mixture was treated as in Example 7 to give (+)-2,2-dimethyl-3-isobutenylcyclopropane-1-carboxylic acid (6.5 g).

EXAMPLE 10

In a 200 ml flask, there were charged levo-rotatory cis- and trans-2,2-dimethyl-3-isobutenylcyclopropane-1-carboxylic acid chloride (composition: (+)-trans, 14.0 % by weight; (−)-trans, 65.8 % by weight; (+)-cis, 2.8 % by weight; (−)-cis, 17.4 % by weight) (9.9 g) and n-hexane (90 g), and stannic chloride (0.7 g) was added thereto. The contents were stirred at 65° to 70° C for 5 hours. The reaction mixture was treated as in Example 7 to give (+)-2,2-dimethyl-3-isobutenylcyclopropane-1-carboxylic acid (6.7 g) (composition: (+)-trans, 43.9 % by weight; (−)-trans, 46.1 % by weight; (+)-cis, 4.4 % by weight; (−)-cis, 4.6 % by weight).

EXAMPLE 11

In a 200 ml flask, there were charged levo-rotatory cis- and trans-2,2-dimethyl-3-isobutenylcyclopropane-1-carboxylic acid chloride (composition: (+)-trans, 13.1 % by weight; (−)-trans, 67.2 % by weight; (+)-cis, 1.9 % by weight; (−)-cis, 17.9 % by weight) (12.4 g) and 1,1,2,2-tetrachloroethane (109 g), and anhydrous aluminum chloride (0.43 g) was added thereto. The contents were stirred at 70° − 72° C for 6 hours. The reaction mixture was treated as in Example 7 to give (+)-2,2-dimethyl-3-isobutenylcyclopropane-1-carboxylic acid (6.8 g) (composition: (+)-trans, 42.1 % by weight; (−)-trans, 48.9 % by weight; (+)-cis, 4.3 % by weight; (−)-cis, 4.8 % by weight).

What is claimed is:

1. A method for the racemization of an optically active 2,2-dimethyl-3-(1′-alkenyl)-cyclopropane-1-carboxylic acid halide of the formula:

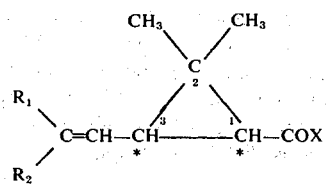

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms and X is a halogen atom, which comprises contacting the acid halide with a Lewis acid in an amount of about 1/2000 to 1/2 mole per 1 mole of the acid halide at a temperature sufficient to permit the racemization to proceed until a trans-rich racemic mixture is obtained.

2. The method according to claim 1, wherein said acid halide is first prepared by converting the corresponding acid to the acid halide prior to contacting the acid halide with said Lewis acid to give said trans-rich mixture.

3. The method according to claim 1, wherein the Lewis acid is a metal halide type Lewis acid.

4. The method according to claim 1, wherein the Lewis acid is aluminum chloride, aluminum bromide, ferric chloride, stannic chloride, titanium chloride, boron trichloride, boron trifluoride or zinc chloride.

5. The method according to claim 1, wherein the contact is effected in an inert solvent.

6. The method according to claim 5, wherein the inert solvent is an ether, an aromatic solvent, an aliphatic hydrocarbon or a halogen-substituted aliphatic hydrocarbon.

7. The method according to claim 1, wherein the contact is effected at a temperature of from about 20° C to the boiling temperature of the reaction system.

8. The method according to claim 1, wherein the contact is effected for about 10 minutes to 20 hours.

9. The method according to claim 1, wherein the acid halide is an acid chloride.

* * * * *